United States Patent [19]

Rabourn

[11] 4,152,348

[45] May 1, 1979

[54] STABILIZED ISOCYANATE COMPOSITIONS

[75] Inventor: Warren J. Rabourn, Deer Park, Tex.

[73] Assignee: The Upjohn Company, Kalamazoo, Mich.

[21] Appl. No.: 880,284

[22] Filed: Feb. 22, 1978

[51] Int. Cl.$^2$ ............... C07C 119/042; C07C 125/06
[52] U.S. Cl. ............................ 260/453 SP; 560/26
[58] Field of Search ................ 260/453 SP, 458 NZ; 560/26

[56] References Cited

U.S. PATENT DOCUMENTS

| | | | |
|---|---|---|---|
| 3,380,959 | 4/1968 | Frump ........................ | 260/45.8 NZ |
| 3,661,861 | 5/1972 | Hunsucker ................... | 260/77.5 R |
| 3,846,419 | 11/1974 | Seeliger et al. ............ | 260/45.8 NZ X |
| 3,914,189 | 11/1975 | Rudner et al. .............. | 260/2.5 AC |

*Primary Examiner*—Dolph H. Torrence

*Attorney, Agent, or Firm*—Denis A. Firth; John Kekich

[57] ABSTRACT

Color stabilized isocyanates, particularly methylene-bridged aromatic isocyanates [methylenebis(phenyl isocyanate) and prepolymers thereof], are derived by incorporating in the isocyanate a color stabilizing amount of a compound of the formula

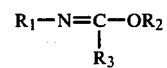

wherein $R_1$ =alkyl, aryl; $R_2$ =alkyl; $R_3$ =H, alkyl or aralkyl; and $R_1$ and $R_2$ taken together represent the residue of an oxazoline or oxazine. 2-Ethyloxazoline is a preferred color stabilizing compound. The above compounds can also be used to discharge undesirable colors which have developed in such isocyanates on storage.

22 Claims, No Drawings

STABILIZED ISOCYANATE COMPOSITIONS

BACKGROUND OF THE INVENTION

1. Field of the Invention

This invention relates to isocyanate compositions and is more particularly concerned with color stabilized organic isocyanates.

2. Description of the Prior Art

The tendency of many organic isocyanates to form undesirable colored impurities on storage is well-known. This is especially true in the case of those compounds which have isocyanate groups attached to aromatic rings which rings are connected by methylene groups. Methylenebis (phenyl isocyanate) is typical of such isocyanates and is a compound which is originally white when obtained by distillation but which, on storage at ambient temperatures or lower, even in the absence of oxygen and sunlight, frequently becomes colored yellow or brown and even green or blue in certain instances. The same phenomenon is observed in the case of various forms of this diisocyanate, such as liquid prepolymers thereof derived by reacting the diisocyanate with a minor amount of an aliphatic diol or mixture of such diols.

Numerous attempts to cure the above problems by the addition of antioxidants and the like have been reported and have met with varying degrees of success. Typical are the processes reported in U.S. Pat. Nos. 2,885,420-6; 2,950,307; 3,585,229 and 3,715,381. We have found, however, that, under certain circumstances, methylenebis(phenyl isocyanates) and related compounds can develop coloration on storage at ambient temperatures even in the presence of relatively large amounts of the antioxidants and other materials employed in the prior art to prevent color formation. We have also found that the prior art antioxidants and additives are not effective in discharging color which has already been formed by impurities in said diisocyanates even though the same additives can inhibit the formation of said coloration if added to the diisocyanate before the coloration has been allowed to occur.

The present invention is based on our discovery that certain alicyclic and heterocyclic compounds containing the grouping

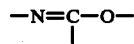

are highly effective in preventing discoloration on storage at ambient temperatures of organic polyisocyanates susceptible to coloration on storage and particularly in respect of methylenebis (phenyl isocyanates) and related compounds. These same alicyclic and heterocyclic compounds can also be used to discharge coloration in said isocyanates after the formation of colored impurities has taken place. Certain of the compounds which are utilized in accordance with the present invention have been reported as useful in catalyzing the reaction between isocyanates and active-hydrogen containing compounds (see U.S. Pat. No. 3,914,189) and in the preparation of isocyanate-terminated prepolymers in the formation of moisture-curable coating compositions (see U.S. Pat. No. 3,661,861). However, it has not been reported previously that very minor amounts of said compounds can be used to stabilize isocyanates against color formation or to discharge color from isocyanates containing colored impurities.

SUMMARY OF THE INVENTION

This invention comprises isocyanate compositions stabilized against color formation on storage at temperatures from about −20° C. to about 50° C., which compositions comprise an organic isocyanate having incorporated therein a color stabilizing amount of a compound having the formula:

wherein $R_1$ is selected from the group consisting of lower-alkyl and aryl, $R_2$ represents lower-alkyl, $R_1$ and $R_2$ taken together represent lower-alkylene having 2 to 3 carbon atoms in the chain which with the

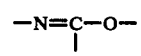

group forms the residue of a heterocyclic ring having from 5 to 6 ring atoms, and $R_3$ represents a group selected from the class consisting of hydrogen, lower-alkyl, and aralkyl.

The invention also comprises a process for stabilizing said isocyanates against color formation as well as for discharging color from said isocyanates in which color formation has already taken place and preventing further color formation therein.

The term "lower-alkyl" means an alkyl radical having from 1 to 8 carbon atoms, inclusive, such as methyl, ethyl, propyl, butyl, pentyl, hexyl, heptyl, octyl and isomeric forms thereof. The term "aryl" means the radical obtained by removing a hydrogen atom from a nuclear carbon atom of an aromatic hydrocarbon containing from 6 to 12 carbon atoms, inclusive. Illustrative of aryl are phenyl, tolyl, xylyl, naphthyl, diphenylyl, and the like. The term "aralkyl" means aralkyl from 7 to 13 carbon atoms, inclusive, such as benzyl, phenethyl, phenylpropyl, naphthylmethyl, benzhydryl and the like. The term "lower-alkylene having 2 to 3 carbon atoms in the chain" means the divalent radical $-C_nH_{2n}-$ wherein there are 2 or 3 carbon atoms in the chain separating the valencies and the hydrogen atoms on each of which carbon atoms can be substituted by alkyl but with the limitation that there are no more than 8 carbon atoms in the alkylene radical. Illustrative of lower-alkylene meeting the above requirements are $-CH_2CH_2-$, $-CH_2CH_2CH_2-$,

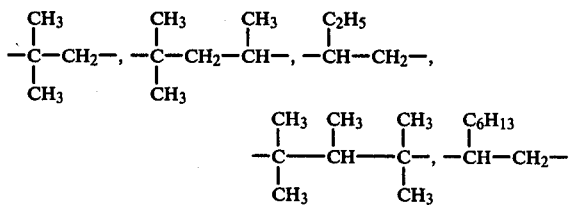

and the like.

DETAILED DESCRIPTION OF THE INVENTION

Illustrative of organic isocyanates which can be decolorized and or stabilized against color formation in accordance with this invention are aryl isocyanates such as phenylisocyanate, tolyl isocyanate, chlorophenyl isocyanate; arylene diisocyanates such as meta or para phenylene diisocyanates, m-xylylene diisocyanate, p-xylylene diisocyanate, naphthalene-1,5-diisocyanate, diphenyl-4,4'-diisocyanate, and tolylene diisocyanate, including mixtures of the 2,4- and 2,6-isomers thereof; diphenylmethane-4,4'-diisocyanate and mixtures thereof containing polyisocyanates of higher functionality, 3-methyldiphenylmethane-4,4'-diisocyanate, chlorophenylene-2,4-diisocyanate; alkylene diisocyanates such as tetramethylene diisocyanate, pentamethylene diisocyanate, hexamethylene diisocyanate, heptamethylene diisocyanate, octamethylene diisocyanate, nonamethylene diisocyanate, decamethylene diisocyanate, dodecamethylene diisocyanate, cyclohexane-1,4-diisocyanate, cyclohexane-1,3-diisocyanate, methylcyclohexane-2,4- and 2,6-diisocyanates, 1,3- and 1,4-bis-(isocyanatomethyl) cyclohexane, diisocyanatodicyclohexylmethane, β-isocyanatoethylphenyl isocyanate, α-isocyanatobenzyl isocyanate; alkyl isocyanates such as methyl isocyanate, ethyl isocyanate, propyl isocyanate, isopropyl isocyanate, butyl isocyanate, amyl isocyanate, hexyl isocyanate, heptyl isocyanate, octyl isocyanate, nonyl isocyanate, decyl isocyanate, dodecyl isocyanate, cyclohexyl isocyanate, chlorohexyl isocyanate, and the like.

The compositions of the invention are derived by incorporating the appropriate color stabilizing amount of the compound (I), or a mixture of two or more compounds of formula (I), in the isocyanate which is to be decolorized and or color stabilized. The mixing of the components can be achieved by any of the mixing processes conventional in the art. In the case of isocyanates such as methylenebis(phenyl isocyanates), particularly those which contain the 4,4'-isomer as the major component, which are normally solid at room temperature (circa 20° C.) it is advantageous to melt these isocyanates by heating to a temperature at or above the melting point (circa 40°-43° C. depending on the isomer distribution) prior to admixture with the compound (I). Alternatively, the admixture can be accomplished by mixing the isocyanate in the solid state with the compound (I) using a ball mill, hammer mill, micronizing machine and the like. In the case of the prepolymers of the methylenebis(phenyl isocyanate), which are generally liquid at ambient temperature, the admixture with the compound (I) is relatively easy.

The amount of compound (I), or mixture of two or more compounds of the formula (I), which it is necessary to add to any particular isocyanate composition to achieve color stabilization, will vary depending upon the particular choice of compound (I) and isocyanate. The most appropriate amount to employ in any given instance can be determined routinely by a process of trial and error. In general it is found that the amount of compound (I), or, when a combination of two or more compounds of formula (I) is used, the total combined amount of said compounds, required to achieve color stabilization, is within the range of about 0.002 weight percent to about 1.0 weight percent based on the weight of isocyanate to be treated. Higher amounts can be used if desired but generally contribute no additional color stabilizing effect while adding significantly to the cost of the stabilized product. A preferred range of amounts of compound (I), or of a combination of such compounds, is from about 0.01 percent by weight to about 0.10 percent by weight based on weight of isocyanate to be treated.

Although the color stabilizing process of the invention can be applied to a wide variety of isocyanates, as set forth above, it is particularly useful in the treatment of methylenebis(phenyl isocyanates). The latter isocyanates can be in the form of any of the various mixtures of the 2,2'-, 2,4'- and 4,4'-isomers known in the art. Such products include the substantially pure 4,4'-isomer, which contains of the order of 98 percent by weight or higher of the 4,4'-isomer, the remainder being 2,4'-isomer with a trace of 2,2'-isomer, as well as mixtures which contain much lower proportions of 4,4'-isomer with correspondingly larger proportions of 2,4'-isomer and 2,2'-isomer. Illustrative of the latter mixtures are those which are described in U.S. Pat. No. 3,362,979 and British Pat. No. 1,422,056.

The methylenebis(phenyl isocyanates) which can be color stabilized in accordance with the present invention also include methylenebis(phenyl isocyanates) which have been reacted with a minor amount, generally less than about 0.2 equivalents per equivalent of isocyanate, of an aliphatic glycol or mixture of such glycols to form products which are liquid at room temperature. Illustrative of such products are those described in U.S. Pat. Nos. 3,394,164; 3,394,165; 3,644,457; and 3,883,571. The first two named patents describe liquid compositions prepared by reacting methylenebis(phenyl isocyanate) with up to 10 percent by weight of dipropylene glycol and di(2-hydroxypropyl-)aniline, respectively. The third named patent describes liquid compositions prepared by reacting methylenebis(phenyl isocyanate) with from 0.1 to 0.3 mole, per mole of isocyanate, of a polypropylene glycol of which tripropylene glycol is typical. The last named patent describes liquid compositions prepared by reacting from 15 to 30 percent of the isocyanate groups of methylenebis(phenyl isocyanate) with a mixture of three alkylene glycols selected from diethylene glycol, triethylene glycol, tetramethylene glycol, 1,2-propylene glycol, 1,3-propylene glycol, neopentyl glycol, 1,3-butanediol, and 1,2-butanediol. The various glycols are employed in such proportions that no one glycol constitutes more than 50 or less than 25 molar percent of the total glycol mixture.

The above types of liquid methylenebis(phenyl isocyanates) frequently have a tendency to develop a green or blue color on storage at ambient temperatures (circa 20°-30° C.) for reasons which are not clearly understood. It has been found that formation of such color on storage at ambient temperatures or below (down to about −20° C.) can be prevented by incorporation of a compound of formula (I), or a mixture of such compounds, in the proportions set forth above. It has further been found that compositions in which such colors have already been formed as a result of storage can be freed of said coloration by the addition of a compound of formula (I), or a mixture of such compounds, in proportions within the ranges set forth above. Further, the compositions so treated are thereby stabilized against any further formation of color on storage for prolonged periods at ambient temperatures or below.

Illustrative of compounds of the formula (I) are alkyl N-(aryl) imidates such as methyl N-phenylformimidate, ethyl N-phenylformimidate, ethyl N-tolylformimidate, ethyl N-phenylacetimidate, ethyl N-phenylpropionimidate, methyl N-phenylbutyrimidate, ethyl N-(p-tert.- butylphenyl)formimidate and the like; oxazolines such as 2-methyl-, 2-ethyl-, 2,4,4-trimethyl-, 2-benzyl-, 2-hexyl-, 2-octyl-, 2-ethyl-4-methyl-, and 2-propyl-4,4-dimethyl-oxazolines and the like; and oxazines such as 2-benzyl-5,6-dihydro-4,4, 6-trimethyl-, 6-butyl-5,6-dihydro-2-methyl-, 5,6-dihydro-2,6-dimethyl-, 5,6-dihydro-6,6-dimethyl-, and 5,6-dihydro-2,5,5,6,6,-pentamethyl-4H-1,3-oxazine, and the like. All the above compounds and classes of compounds are known in the art and can be prepared by methods well-described in the art.

A preferred group of compounds of formula (I) are the alkyl substituted oxazolines and a particularly preferred species within this group is 2-ethyloxazoline.

The compositions of the invention can be stored at temperatures ranging from about $-20°$ C. to about $50°$ C. for prolonged periods (and up to about $80°$ C. for short periods) and remain substantially free of color formation even if color was originally present in the isocyanate component and was discharged by addition of the compound (I) or a mixture of such compounds. Further, it is found that the presence of the compound (I), or a mixture of such compounds, in the isocyanate compositions of the invention does not interfere in any way with the ultimate usefulness of the isocyanate compositions. Thus, the isocyanate compositions of the invention can be used for all the same purposes as the same isocyanates free of the compound (I). Further, the presence of the latter in compositions derived from polyisocyanates does not affect the manner in which the polyisocyanates react in any of the multitude of polymer syntheses for which polyisocyanates such as methylenebis(phenyl isocyanates) are currently employed.

In a further aspect of the invention, I have found that the upper limit of the range of temperature ($-20°$ C. to about $50°$ C.) at which organic isocyanates treated with a compound of the formula (I) will remain stabilized against color formation can be significantly increased (to about $80°$ C. or even higher in certain cases) by employing certain stabilizers already known in the art in combination with the compound of formula (I) or mixture of two or more of the latter compounds. Thus, I have found that a combination of a compound of formula (I) with minor amounts of triphenyl phosphite and 2,6-di-tert.-butyl-4-methylphenol imparts color stability to organic isocyanates over an increased range of temperature ($-20°$ C. to $80°$ C. or above) than can be achieved by the use of any of these stabilizing compounds alone. Thus, a combination of triphenyl phosphite and 2,6-di-tert.-butyl-4-methylphenol is not generally effective in stabilizing isocyanates against color formation in the lower end of the above range and the ability of this combination to stabilize color at the higher end of the range is enhanced by the use of the compound (I). In this aspect of the invention the amount of compound (I) which is employed in the color stabilized isocyanate compositions is within the range set forth above and the amounts of the other two compounds are advantageously within the range of about 0.01 percent to about 0.2 percent by weight based on isocyanate. The use of the above combination of stabilizers does not in any way detract from the reactivity or other behaviour of the so stabilized isocyanates when the latter are employed in reactions conventional in the art for such isocyanates.

The following examples describe the manner and process of making and using the invention and set forth the best mode contemplated by the inventors of carrying out the invention but are not to be construed as limiting.

EXAMPLE 1

A series of isocyanate compositions was prepared from a mixture of methylenebis(phenyl isocyanates) containing 93.6 percent by weight of 4,4'-isomer and 6.4% 2,4'-isomer. A sample of the starting material was maintained as control while three other equal samples of the starting material were melted and blended with 0.01% by weight of 2-ethyloxazoline, 0.1% by weight of 2-ethyloxazoline, and 0.1% by weight of 2-ethyl-N-phenylformimidate, respectively. The control and the three samples were maintained in containers (purged initially with nitrogen) for 4 weeks at 0° C. Analytical data determined for each of the samples immediately after admixture with the inhibitors and again at the end of the storage period are shown in Table I. Comparison of the amount of absorption at two frequencies (426 and 500 nm) in the visible spectra were determined using a Perkin-Elmer 200 instrument on the initial samples, then after 1 week's storage and again after the storage period was complete. The results are shown in Table II. The ratio ($A_1/A_0$ and $A_4/A_0$) of absorption after storage to initial absorption shows that, in the case of each of the inhibitors, the amount of absorption at both test frequencies had decreased substantially in the case of the three treated samples, whereas the amount of absorption at both frequencies had increased substantially in the case of the control. At the end of the storage period the control sample was orange-yellow in color while the other samples were white.

TABLE I

| Analytical Data on Samples Stored at 0° C. | | | | | | | | |
|---|---|---|---|---|---|---|---|---|
| | Control | | 0.01% 2-ethyloxazoline | | 0.1% 2-ethyloxazoline | | 0.1% Ethyl N-phenylformimidate | |
| | Initial | 4 Weeks | 1 Week | 4 Weeks | 1 Week | 4 Weeks | 1 Week | 4 Weeks |
| Isocyanate equivalent | 125.4 | 125.6 | 125.9 | 125.5 | 126.2 | 125.8 | — | 125.5 |
| Total hydrolyzable chloride (ppm) | 81 | 87 | 100 | 80 | 89 | 88 | — | 80 |
| Hydrolyzable chloride (ppm) | 44 | 52 | 36 | 52 | 44 | 51 | — | 49 |
| % dimer (w/w) | 0.54 | 0.34 | 0.40 | 0.39 | 0.39 | 0.40 | — | 0.38 |
| 4,4'-isomer % w/w | 93.6 | 93.2 | 92.2 | 92.9 | 92.0 | 92.5 | — | 91.7 |
| 2,4'-isomer % w/w | 6.4 | 6.8 | 7.8 | 7.1 | 8.0 | 7.5 | — | 8.3 |

TABLE II

| | Absorption Data on Samples Stored at 0° C. | | | | | | | | | |
|---|---|---|---|---|---|---|---|---|---|---|
| | Absorption at 426 nm | | | | | Absorption at 500 nm | | | | |
| | Initial $A_0$ | 1 Week $A_1$ | $A_1/A_0$ | 4 Weeks $A_4$ | $A_4/A_0$ | Initial $A_1$ | 1 Week $A_0$ | $A_1/A_4$ | 4 Weeks $A_0$ | $A_4/A_0$ |
| Control | 0.044 | — | — | 1.08 | 24.50 | 0.015 | — | — | 0.140 | 9.33 |
| + 0.01% 2-ethyl-oxazoline | 0.044 | 0.048 | 1.09 | 0.033 | 0.75 | 0.015 | 0.016 | 1.07 | 0.008 | 0.53 |
| + 0.1% 2-ethyl-oxazoline | 0.044 | 0.037 | 0.84 | 0.013 | 0.30 | 0.015 | 0.005 | 0.33 | 0.003 | 0.20 |
| + 0.1% ethyl N-phenylformimidate | 0.044 | — | — | 0.023 | 0.52 | 0.015 | — | — | 0.010 | 0.67 |

EXAMPLE 2

The experiment described in Example 1 was repeated but using as starting material a methylenebis(phenyl isocyanate) containing 98.6% by weight of 4,4'-methylenebis(phenyl isocyanate) and 1.4% by weight of 2.4'-methylenebis(phenyl isocyanate), and extending the storage period at 0° C. to 24 weeks. The analytical results on the samples before and after storage are shown in Table III and the absorption at 440 nm and 540 nm before and after storage at 0° C. are shown in Table IV.

TABLE III

| | Analtical Data on Samples Stored at 0° C. | | | | | | | |
|---|---|---|---|---|---|---|---|---|
| | Control | | 0.01% 2-ethyl-oxazoline | | 0.1% 2-ethyl-oxazoline | | 0.1% Ethyl N-phenylformimidate | |
| | 1 Week | 24 Weeks | 1 Week | 24 Weeks | 1 Week | 24 Weeks | 1 Week | 24 Weeks |
| Isocyanate equivalent | 125.9 | 125.2 | 126.3 | 125.5 | 126.8 | 125.8 | 126.9 | 124.5 |
| Total hydrolyzable chloride (ppm) | 47 | 34 | 26 | 45 | 31 | 44 | 29 | 37 |
| Hydrolyzable chloride (ppm) | 23 | 6 | 4 | 17 | 8 | 6 | 13 | 18 |
| % dimer | 0.38 | 0.48 | 0.37 | 0.38 | 0.40 | 0.51 | 0.38 | 0.37 |

TABLE IV

| | Absorption Data on Samples Stored at 0° C. | | | | | | | | | |
|---|---|---|---|---|---|---|---|---|---|---|
| | Absorption at 440 nm | | | | | Absorption at 540 nm | | | | |
| | Initial $A_0$ | 1 Week $A_1$ | $A_1/A_0$ | 24 Weeks $A_{24}$ | $A_{24}/A_0$ | Initial $A_0$ | 1 Week $A_0$ | $A_1/A\text{ hd }24$ | 24 Weeks $A_0$ | $A_{24}/A_0$ |
| Control | 0.016 | 0.09 | 5.62 | 0.151 | 9.43 | 0.004 | 0.006 | 1.5 | 0.010 | 2.5 |
| + 0.01% 2-ethyl-oxazoline | 0.016 | 0.062 | 3.87 | 0.120 | 7.5 | 0.004 | 0.008 | 2.0 | 0.011 | 2.75 |
| + 0.1% 2-ethyl-oxazoline | 0.016 | 0.010 | 0.62 | 0.011 | 0.68 | 0.004 | 0.000 | 0 | 0.000 | 0 |
| + 0.1% Ethyl N-phenylformimidate | 0.016 | 0.014 | 0.87 | 0.004 | 0.25 | 0.004 | 0.004 | 1 | 0.003 | 0.75 |

At the end of the storage period the control sample was amber colored while the various treated samples were clear and colorless.

EXAMPLE 3

The experiment described in Example 2 was repeated exactly as described except that all samples were stored at 45° C. instead of 0° C. for the duration of the test. The results are shown in Tables V and VI below.

TABLE V

| | Analytical Data on Samples Stored at 45° C. | | | | | | | |
|---|---|---|---|---|---|---|---|---|
| | Control | | 0.01% 2-ethyl-oxazoline | | 0.1% 2-ethyl-oxazoline | | 0.1% Ethyl N-phenylformimidate | |
| | 1 Week | 24 Weeks | 1 Week | 24 Weeks | 1 Week | 24 Weeks | 1 Week | 24 Weeks |
| Isocyanate equivalent | 125.2 | 125.6 | 126.3 | 125.4 | 125.9 | 125.8 | 125.7 | a 125.8 |
| Total hydrolyzable chloride (ppm) | 42 | 65 | 38 | 44 | 40 | 50 | 28 | 39 |
| Hydrolyzable Chloride (ppm) | 12 | 39 | 16 | 40 | 10 | 39 | 10 | 37 |
| % dimer w/w | 0.55 | 0.56 | 0.46 | 0.59 | 0.53 | 0.64 | 0.46 | 0.57 |

TABLE VI

| | Absorption Data on Samples Stored at 45° C. | | | | | | | | | |
|---|---|---|---|---|---|---|---|---|---|---|
| | Absorption at 440 nm | | | | | Absorption at 540 nm | | | | |
| | Initial $A_0$ | 1 Week $A_1$ | $A_1/A_0$ | 24 Weeks $A_{24}$ | $A_{24}/A_0$ | Initial $A_0$ | 1 Week $A_1$ | $A_1/A_0$ | 24 Weeks $A_{424}$ | $A_{24}/A_0$ |
| Control | 0.016 | 0.020 | 1.25 | 0.013 | 0.812 | 0.004 | 0.003 | 0.75 | 0.002 | 0.5 |
| 0.01% 2-ethyl-oxazoline | 0.016 | 0.026 | 1.62 | 0.014 | 0.875 | 0.004 | 0.004 | 1.0 | 0.001 | 0.25 |

TABLE VI-continued

| | Absorption Data on Samples Stored at 45° C. | | | | | | | | | |
| | Absorption at 440 nm | | | | | Absorption at 540 nm | | | | |
| | Initial $A_0$ | 1 Week $A_1$ | $A_1/A_0$ | 24 Weeks $A_{24}$ | $A_{24}/A_0$ | Initial $A_0$ | 1 Week $A_1$ | $A_1/A_0$ | 24 Weeks $A_{A24}$ | $A_{24}/A_0$ |
|---|---|---|---|---|---|---|---|---|---|---|
| 0.1% 2-ethyl-oxazoline | 0.016 | 0.022 | 1.37 | 0.005 | 0.312 | 0.004 | 0.001 | 0.25 | 0.000 | 0 |
| 0.1% Ethyl N-phenylformimidate | 0.016 | 0.020 | 1.25 | 0.011 | 0.687 | 0.004 | 0.001 | 0.25 | 0.001 | 0.25 |

At the end of the storage period the control sample was light yellow colored and the various treated samples were clear and colorless.

EXAMPLE 4

The methylenebis(phenyl isocyanate) employed as starting material in Example 2 was employed to prepare the following compositions. Three 10 g. aliquots of the isocyanate were meltled and blended with 0.1 g. of one of 2-benzyl-5,6-dihydro-4,4,6-trimethyl-4H-1,3-oxaine, 2-methyloxazoline and 2,4,4-trimethyloxazoline, respectively. The three samples and an untreated sample of the starting isocyanate were stored at 0° C. for 2 weeks. At the end of this time it was found that the three treated samples were still white whereas the control (untreated) sample was yellow to amber colored.

EXAMPLE 5

The isocyanate used as starting material was a liquid material of isocyanate equivalent 180 which had been obtained by reacting 1 equivalent of methylenebis(phenyl isocyanate) containing 98.2% w/w 4,4'-isomer and 1.8% w/w 2,4'-isomer with 0.123 equivalents of dipropylene glycol and 0.093 equivalents of tripropylene glycol. The isocyanate had developed a bluish green color shortly after its preparation. To a batch of 2220 g. of this material was added slowly with stirring a total of 200 microliters (0.20 g.) of 2-ethyloxazoline. The bluish green color disappeared substantially instantaneously when the addition was complete and the resulting product remained colorless after standing at ambient temperature (20°-25° C.) under an atmosphere of nitrogen for a prolonged period.

EXAMPLE 6

This example illustrates the use of a combination of 2-ethyloxazoline with triphenylphosphite and 2,6-di-tert.-butyl-4-methylphenol in stabilizing an organic isocyanate against color formation on storage at 80° C.

Using a methylenebis(phenyl isocyanate) of the same composition as that employed in Example 2 there was prepared an isocyanate composition containing 0.05 percent by weight of 2-ethyloxazoline, 0.09 percent by weight of 2,6-di-tert.-butyl-4-methylphenol and 0.159 percent by weight of triphenylphosphite. Aliquots of this composition were stored at 0° C., ambient temperature (20°-25° C.), 50° C. and 80° C. for four weeks. At the end of this time all four aliquots were found to have remained colorless.

I claim:

1. An isocyanate composition stabilized against color formation which comprises an organic isocyanate, which is normally susceptible to color formation on storage, having incorporated therein a color stabilizing amount of a compound having the formula

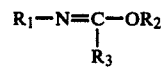

wherein $R_1$ is selected from the group consisting of lower-alkyl and aryl, having from 6 to 12 carbon atoms, inclusive, $R_2$ represents lower-alkyl, $R_1$ and $R_2$ taken together represent lower-alkylene having 2 to 3 carbon atoms in the chain which with the

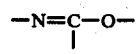

group forms the residue of a heterocyclic ring containing from 5 to 6 ring atoms and $R_3$ represents a group selected from the class consisting of hydrogen, lower-alkyl, and aralkyl having from 7 to 13 carbon atoms, inclusive.

2. A composition according to claim 1 wherein said isocyanate contains a color stabilizing amount of 2-ethyloxazoline.

3. A composition according to claim 1 wherein said isocyanate contains a color stabilizing amount of ethyl N-phenylformimidate.

4. A composition according to claim 1 wherein said isocyanate contains a color stabilizing amount of 2-benzyl-5,6-dihydro-4,4,6-trimethyl-4H-1,3-oxazine.

5. A composition according to claim 1 wherein said isocyanate contains a color stabilizing amount of 2-methyloxazoline.

6. A composition according to claim 1 wherein said isocyanate contains a color stabilizing amount of 2,4,4-trimethyloxazoline.

7. A composition according to claim 1 wherein said isocyanate is methylenebis(phenyl isocyanate).

8. A composition according to claim 1 wherein said isocyanate is a prepolymer of methylenebis(phenyl isocyanate) and an aliphatic diol.

9. An isocyanate composition stabilized against color formation which comprises an organic isocyanate selected from methylenebis(phenyl isocyanate) and prepolymers thereof with aliphatic diols, said isocyanate having incorporated therein a color stabilizing amount of a compound having the formula:

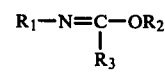

wherein $R_1$ is selected from the group consisting of lower-alkyl and aryl, having from 6 to 12 carbon atoms, inclusive, $R_2$ represents lower-alkyl, $R_1$ and $R_2$ taken together represent lower-alkylene having 2 to 3 carbon atoms in the chain which with the

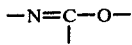

group forms the residue of a heterocyclic ring containing from 5 to 6 ring atoms, and $R_3$ represents a group selected from the class consisting of hydrogen, lower-alkyl, and aralkyl having from 7 to 13 carbon atoms, inclusive.

10. A composition according to claim 9 wherein the color stabilizing compound is 2-ethyloxazoline.

11. A composition according to claim 9 wherein the color stabilizing compound is ethyl N-phenylformimidate.

12. A composition according to claim 9 wherein the color stabilizing compound is 2-benzyl-5,6-dihydro-4,4,6-trimethyl-4H-1,3-oxazine.

13. A composition according to claim 9 wherein the color stabilizing compound is 2-methyloxazoline.

14. A composition according to claim 9 wherein the color stabilizing compound is 2,4,4-trimethyloxazoline.

15. A composition according to claim 9 which also comprises color stabilizing amounts of triphenyl phosphite and 2,6-di-tert.-butyl-4-methylphenol.

16. A composition stabilized against the formation of color comprising 4,4'-methylenebis(phenyl isocyanate) and a color stabilizing amount of 2-ethyloxazoline.

17. A composition according to claim 16 which also comprises color stabilizing amounts of triphenyl phosphite and 2,6-di-tert.-butyl-4-methylphenol.

18. A composition stabilized against the formation of color comprising 4,4'-methylenebis(phenyl isocyanate) and a color stabilizing amount of 2-methyloxazoline.

19. A process for discharging the color which has formed on storage of an aromatic isocyanate containing a methylene group bridging two aromatic nuclei which process comprises incorporating into said isocyanate a color discharging quantity of a compound having the formula:

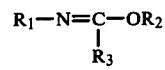

wherein $R_1$ is selected from the group consisting of lower-alkyl and aryl, $R_2$ represents lower-alkyl, $R_1$ and $R_2$ taken together with the

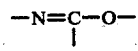

group to which they are attached form the residue of a heterocyclic ring selected from oxazoline and oxazine, and $R_3$ represents a group selected from the class consisting of hydrogen, lower-alkyl, and aralkyl having from 7 to 13 carbon atoms, inclusive.

20. A process according to claim 19 wherein said color discharging compound is 2-ethyloxazoline.

21. A process according to claim 19 wherein said aromatic isocyanate is 4,4'-methylenebis(phenyl isocyanate).

22. A process according to claim 19 wherein said aromatic isocyanate is a prepolymer of 4,4'-methylenebis(phenyl isocyanate) and at least one aliphatic diol.

* * * * *

UNITED STATES PATENT OFFICE
CERTIFICATE OF CORRECTION

Patent No. 4,152,348　　　　　　　　Dated May 1, 1979

Inventor(s)　Warren J. Rabourn

It is certified that error appears in the above-identified patent and that said Letters Patent are hereby corrected as shown below:

Columns 7 and 8, TABLE II:

| Absorption at 500 nm | | | | |
|---|---|---|---|---|
| Initial | 1 week | $A_1/A_0$ | 4 weeks | $A_4/A_0$ |
| $A_1$ | $A_0$ | $A_4$ | $A_0$ | |

Should read:

| Absorption at 500 nm | | | | |
|---|---|---|---|---|
| Initial | 1 week | $A_1/A_0$ | 4 weeks | $A_4/A_0$ |
| $A_0$ | $A_1$ | | $A_4$ | |

Columns 7 and 8, TABLE IV:

| Absorption at 540 nm | | | | |
|---|---|---|---|---|
| Initial | 1 week | $A_1/A_{24}$ hd | 24 weeks | $A_{24}/A_0$ |
| $A_0$ | $A_0$ | | $A_0$ | |

(Cont'd. next page)

UNITED STATES PATENT OFFICE
CERTIFICATE OF CORRECTION

Patent No. 4,152,348      Dated May 1, 1979

Inventor(s) Warren J. Rabourn

It is certified that error appears in the above-identified patent and that said Letters Patent are hereby corrected as shown below:

Columns 7 and 8, TABLE IV:  Should read:

| Absorption at 540 nm | | | | |
|---|---|---|---|---|
| Initial | 1 week | $A_1/A_0$ | 24 weeks | $A_{24}/A_0$ |
| $A_0$ | $A_1$ | | $A_{24}$ | |

Columns 7 and 8, TABLE V:  Should read:

| 0.1% Ethyl N-phenylformimidate | |
|---|---|
| 1 week | 24 weeks |
| 125.7 | a 125.8 |

| 0.1% Ethyl N-phenylformimidate | |
|---|---|
| 1 week | 24 weeks |
| 125.7 | 125.8 |

Columns 7 and 8 and Columns 9 and 10, TABLE VI:  Should read:

| Absorption at 540 nm |
|---|
| 24 Weeks |
| $A_{124}$ |

| Absorption at 540 nm |
|---|
| 24 Weeks |
| $A_{24}$ |

UNITED STATES PATENT OFFICE
CERTIFICATE OF CORRECTION

Patent No. 4,152,348          Dated May 1, 1979

Inventor(s) Warren J. Rabourn

It is certified that error appears in the above-identified patent and that said Letters Patent are hereby corrected as shown below:

Column 9, line 22:          Should read:

meltled          melted

Column 12, Claim 19, line 16:          Should read:

aryl, $R_2$          aryl, having from 6 to 12 carbon atoms, inclusive, $R_2$

Signed and Sealed this

Twenty-first Day of August 1979

[SEAL]

Attest:

Attesting Officer

LUTRELLE F. PARKER
*Acting Commissioner of Patents and Trademarks*